(12) United States Patent
Loder (10) Patent No.: US 11,514,732 B2
(45) Date of Patent: Nov. 29, 2022

(54) ELECTRICAL MACHINE MONITOR

(71) Applicant: Rolls-Royce Corporation, Indianapolis, IN (US)

(72) Inventor: David Loder, Carmel, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 463 days.

(21) Appl. No.: 16/803,382

(22) Filed: Feb. 27, 2020

(65) Prior Publication Data
US 2021/0272396 A1 Sep. 2, 2021

(51) Int. Cl.
| G07C 5/08 | (2006.01) |
| B64F 5/60 | (2017.01) |
| G07C 5/10 | (2006.01) |
| B60L 3/12 | (2006.01) |
| G01K 7/16 | (2006.01) |
| G01N 33/00 | (2006.01) |
| G01L 11/00 | (2006.01) |

(52) U.S. Cl.
CPC ............ *G07C 5/0816* (2013.01); *B60L 3/12* (2013.01); *B64F 5/60* (2017.01); *G07C 5/0808* (2013.01); *G07C 5/10* (2013.01); *B60L 2200/10* (2013.01); *G01K 7/16* (2013.01); *G01L 11/00* (2013.01); *G01N 33/0004* (2013.01)

(58) Field of Classification Search
CPC ...... G07C 5/0816; G07C 5/0808; G07C 5/10; B64F 5/60; B60L 3/12; B60L 2200/10; G01K 7/16; G01L 11/00; G01N 33/0004
USPC ...................................................... 701/33.6
See application file for complete search history.

(56) References Cited

U.S. PATENT DOCUMENTS

| 9,435,661 | B2 * | 9/2016 | Brenner | G05D 1/0808 |
| 9,937,803 | B2 | 4/2018 | Siegel et al. | |
| 9,975,644 | B1 * | 5/2018 | Kimchi | B64C 39/024 |
| 2016/0297416 | A1 * | 10/2016 | Geller | B60W 20/00 |
| 2018/0079515 | A1 | 3/2018 | Harwood et al. | |
| 2019/0108691 | A1 * | 4/2019 | Tucker | G07C 5/006 |
| 2020/0331628 | A1 * | 10/2020 | Shamasundar | G08G 5/0021 |

OTHER PUBLICATIONS

Iris Power—Partial Discharge Monitoring, Retrieved on Jan. 8, 2020 from https://irispower.com/monitoring/partial-discharge-pd-monitoring/, 8 pgs.

* cited by examiner

*Primary Examiner* — Gertrude Arthur Jeanglaude
(74) *Attorney, Agent, or Firm* — Shumaker & Sieffert, P.A.

(57) ABSTRACT

An example method includes receiving, by one or more processors and via a sensor, a signal representing operational characteristics of a device included in an aircraft; determining, by the one or more processors and based on the signal, a partial discharge intensity value; receiving, by the one or more processors and via an environmental sensor, at least one environmental measurement of the device; modifying, by the one or more processors and based on the at least one environmental measurement, the partial discharge intensity value to determine a modified partial discharge intensity value; and responsive to determining that the modified partial discharge intensity value satisfies a threshold, outputting an alert signal for the device.

20 Claims, 6 Drawing Sheets

ELECTRICAL MACHINE MONITOR

TECHNICAL FIELD

The disclosure relates to electrical machine monitoring.

BACKGROUND

Partial discharge monitoring may be used to manage the insulation health of rotating machinery. Partial discharge monitoring may be used to schedule maintenance and inspections of insulation health in advance of a failure, which can avoid delays in operations and can be critical for rotating machinery whose failure would be highly detrimental to operations.

SUMMARY

In some examples, the disclosure describes a method comprising receiving, by one or more processors and via a sensor, a signal representing operational characteristics of a device included in an aircraft. The method further comprises determining, by the one or more processors and based on the signal, a partial discharge intensity value, and receiving, by the one or more processors and via an environmental sensor, at least one environmental measurement of the device. The method further comprises modifying, by the one or more processors and based on the at least one environmental measurement, the partial discharge intensity value to determine a modified partial discharge intensity value, and responsive to determining that the modified partial discharge intensity value satisfies a threshold, outputting an alert signal for the device.

In some examples, the disclosure describes a system comprising a device included in an aircraft, an environmental sensor, and a sensor. The system further comprises one or more processors configured to receive, via the sensor, a signal representing operational characteristics of a device included in an aircraft, and determine, based on the signal, a partial discharge intensity value. The one or more processors are further configured to receive, via the environmental sensor, at least one environmental measurement of the device. The one or more processors are further configured to modify, based on the at least one environmental measurement, the partial discharge intensity value to determine a modified partial discharge intensity value, and responsive to determining that the modified partial discharge intensity value satisfies a threshold, output an alert signal for the device.

In some examples, the disclosure describes a variable frequency drive system comprising an electric machine, one or more conductor coils, an environmental sensor, and a sensor. The variable frequency drive system further comprises at least one variable frequency drive configured to provide electrical power to the electric machine, the at least one variable frequency drive comprising at least one high voltage terminal and at least one processor. The at least one processor is configured to receive, via the sensor, a signal representing operational characteristics of the variable frequency drive system and determine, based on the signal, a partial discharge intensity value. The at least one processor is further configured to receive, via the environmental sensor, at least one environmental measurement of the variable frequency drive system. The at least one processor is further configured to modify, based on the at least one environmental measurement, the partial discharge intensity value to determine a modified partial discharge intensity value, and, responsive to determining that the modified partial discharge intensity value satisfies a threshold, output an alert signal for the device.

The details of one or more examples are set forth in the accompanying drawings and the description below. Other features, objects, and advantages will be apparent from the description and drawings, and from the claims.

DETAILED DESCRIPTION

Electric machines covert between electrical energy and mechanical energy. As one example, an electric machine may operate as a generator that converts mechanical energy into electrical energy. As another example, an electric machine may operate as an electrical motor that converts electrical energy into mechanical energy. Electric machines typically include a rotor that rotates within a stator. Energy flows through the stator to or from the rotor. In an electric motor, the stator provides a rotating magnetic field that drives the rotor. In a generator, the stator converts the rotating magnetic field to electric energy.

Electric machines may include high voltage electrical conductors in the stator, rotor, or both. The electrical conductors may include insulating material surrounding the conductor, thereby protecting the conductor and preventing shorts or discharges. Partial discharges may be relatively small electrical current sparks that occur in the high voltage electrical insulation, for example, in small air gaps or voids in or on the surface of the insulation. The electrical conductors may be formed into a coil, or a winding, around a ferromagnetic core. As winding insulation deteriorates (e.g., from coil winding vibration, operation at high temperatures, contamination, etc.), the partial discharge activity may increase, and partial discharge monitoring can be used to detect the primary causes of winding failure.

Partial discharge monitoring may be used in the context of utilities and industrial equipment to manage the insulation health of rotating machinery whose failure would be highly detrimental to operations. Partial discharge monitoring may be used to schedule maintenance and inspections in advance of rotating machinery failure, rather than allowing a failure to cause delays.

High voltage insulation systems in the context of electrified propulsion or other mission critical functions have a need for health monitoring. For instance, a failure in a high voltage insulation system of an electrically propelled aircraft may result in a loss of control of the aircraft. Partial discharge monitoring is further desirable in aerospace systems due to the difficulties with qualification of high voltage insulation systems for an aircraft environment. However, variable frequency drive (VFD) systems or switching power supplies create high frequency interference that may conflict with the typical frequency bands used for detecting partial discharges. High pass filtering may be used to eliminate the switching noise, while maintaining the partial discharge frequencies. However, partial discharges in a low-pressure environment may result in a lower upper cutoff frequency, which may complicate high pass filtering and may increase the difficulty of making robust partial discharge measurements. A monitoring system that tracks partial discharge intensity over time may increase the reliability of a monitoring system ensuring a robust insulation system.

Partial discharge monitoring systems face additional challenges when applied to high voltage aerospace power systems. Additional partial discharge monitoring equipment and the associated power and control cabling may add weight, and the components of partial discharge monitoring equipment may not be able to tolerate harsh aerospace environments, for example, temperature extremes, exposure to fluids, and the like. Furthermore, the interface setup of alert systems may limit the usefulness of monitoring systems when embedded in an aircraft.

In accordance with one or more aspects of this disclosure, a partial discharge monitoring system may be integrated within the relevant machine drive, switching power converter, or other similar electronics assembly which possess data processing capability. Such systems and methods may utilize existing components for the additional purposes of partial discharge monitoring, either by direct use of existing components or by modifying existing components for partial discharge monitoring. Such systems may minimize the additional weight added to enable partial discharge monitoring, the existing components may be already qualified for aerospace environments, and the use of the available converter communication bus interface allows direct alerts to the cockpit of a vehicle and storage of data within the flight computer and/or maintenance tracking systems. In addition, existing connections may be used, thereby reducing or eliminating the need for new power and/or communication cabling and connections, reducing any additional weight and complexity necessary for enabling partial discharge monitoring. In some examples, a partial discharge monitoring system may be an online partial discharge monitoring system, for example, an online partial discharge monitoring system may be integrated within the relevant machine drive configured for use in a machine, such as a motor driven by the machine drive mounted and operation on a vehicle. In some examples, an online partial discharge monitoring system is configured to monitor and/or measure partial discharges during operation of the relevant machine drive.

Figure 1:
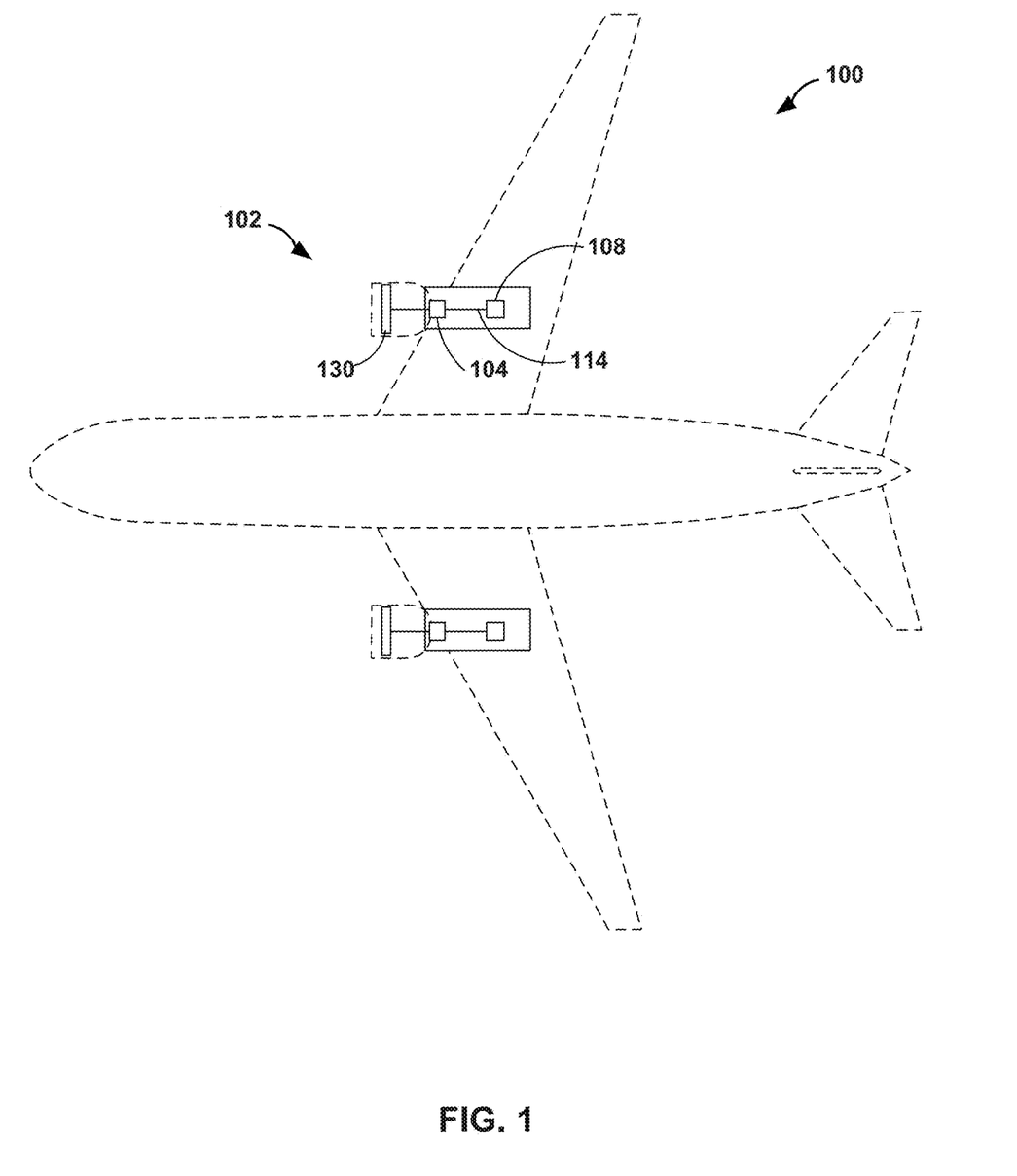
FIG. 1 is a conceptual diagram of a vehicle that includes an electric machine, in accordance with one or more techniques of this disclosure.

FIG. 1 is a conceptual diagram of a vehicle 100 that includes an electric machine including partial discharge monitoring, in accordance with one or more techniques of this disclosure. In some examples, vehicle 100 includes an aircraft. In other examples, vehicle 100 may include any type of vehicle utilizing an electrical machine, including one or more types of air vehicles; land vehicles, including but not limited to, tracked and/or wheeled vehicles; marine vehicles, including but not limited to surface vessels, submarines, and/or semi-submersibles; amphibious vehicles; or any combination of one or more types of air, land, and marine vehicles. Vehicle 100 may be manned, semiautonomous, or autonomous.

As shown in the example of FIG. 1, vehicle 100 may include propulsion system 102. In some examples, propulsion system 102 may include a combustion engine, such as a gas-turbine engine. Propulsion system 102 includes motor 104 that is configured to drive propulsor 130. Propulsion systems that include gas-turbine engines may include an electric starter/generator (ESG) that may both start the gas-turbine engines and generate electrical power using mechanical energy generated by the gas-turbine engines. As shown in FIG. 1, propulsion system 102 may include ESG 108 that is coupled to motor 104 via shaft 114. In some examples, ESG 108 may be configured to provide propulsive energy. For instance, ESG 108 may provide rotational mechanical energy to drive propulsor 130.

In accordance with one or more techniques of this disclosure, vehicle 100 may include components configured to perform partial discharge monitoring of ESG 108. For instance, ESG 108 may include resistance temperature sensors, current transformers and/or sensors, common mode chokes, dV/dt filters, Y-cap EMI filters, environmental sensors, equipment usage sensors, and machine drive modules that may include a processor that receives data from such sensors and determines electrical machine outputs. One or more processors of vehicle 100 may analyze signals generated by the sensors to monitor partial discharges of ESG 108, as described further below.

Figure 2:
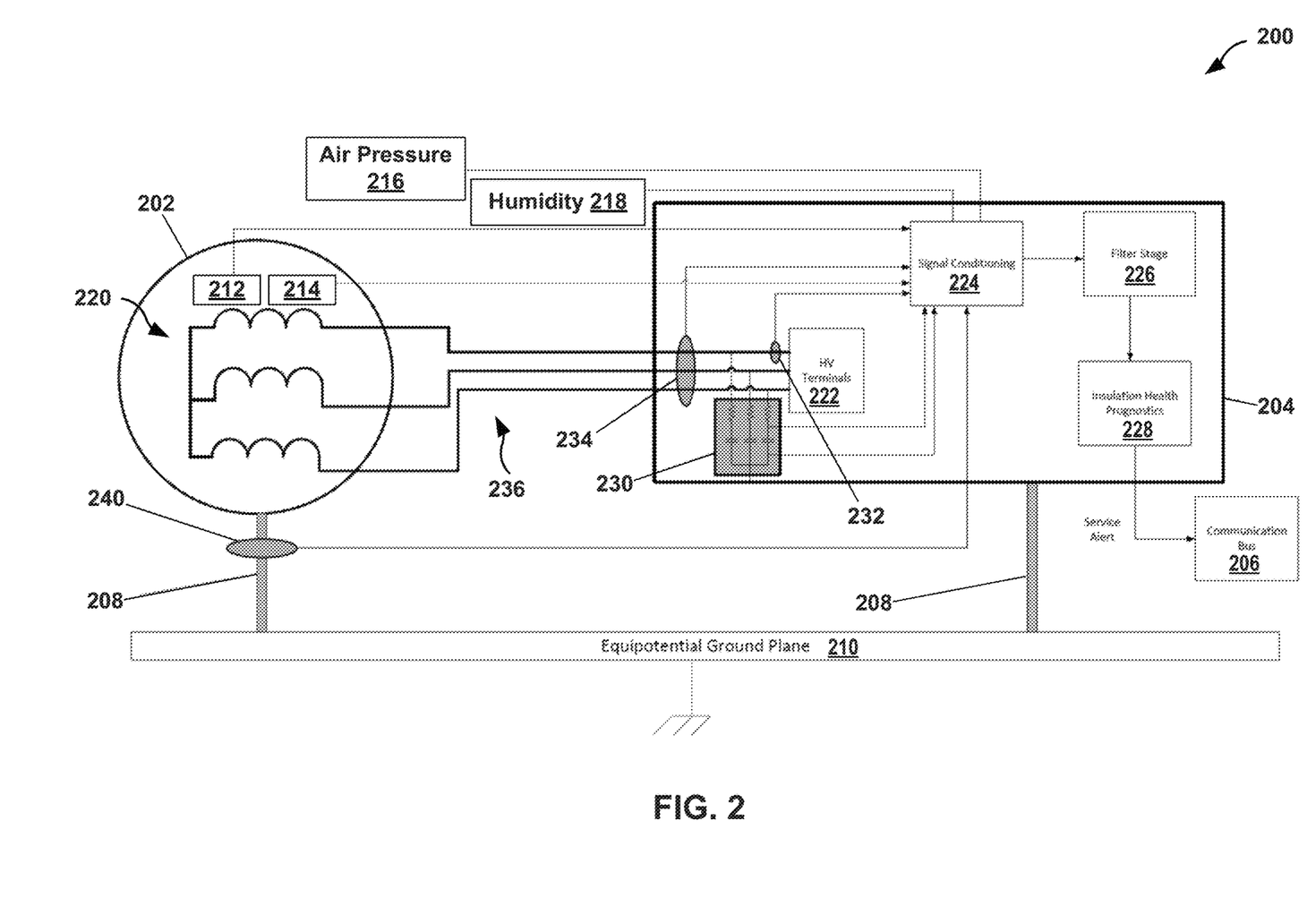
FIG. 2 is a conceptual diagram illustrating an example partial discharge monitoring system, in accordance with one or more techniques of this disclosure.

FIG. 2 is a conceptual diagram illustrating an example partial discharge monitoring system 200, in accordance with one or more techniques of this disclosure. As shown in FIG. 2, system 200 includes an electrical motor/generator 202, a machine drive 204, a communication bus 206, bond straps 208, equipotential ground plane 210, and resistance temperature sensors (RTDs) 212, 214, air pressure sensor 216, and humidity sensor 218. In other examples, system 200 may include additional sensors or omit some of the sensors 212-218.

Electrical motor/generator 202 may include electrical conductors 220, alternatively termed "windings," 220 in either a stator, a rotor, or both. Electrical motor/generator 202 may be considered an example of ESG 108 of FIG. 1. In the example shown, electrical motor/generator 202 includes a three phase high voltage windings 220 construction. Electrical motor/generator 202 may also include resistance temperature sensors (RTDs) 212 and 214. RTDs 212 and 214 may be configured to sense the temperature at one or more areas or components of electrical motor/generator 202 and may be configured to output a voltage proportional to temperature to machine drive 204. Machine drive 204 may be configured to monitor the voltage output by RTDs 212 and 214 to detect overheating of the electrical motor/generator 202. In some examples, the voltage output by RTDs 212 and 214 may include high frequency components corresponding to partial discharge pulses which may be monitored to provide a partial discharge measurement.

In the example shown, machine drive 204 includes high voltage terminals 222, signal conditioning module 224, filter stage 226, and insulation health prognostics module 228. Machine drive 204 may also include dV/dt filter 230, differential mode filter 232, and common mode choke 234. Machine drive 204 may also include processing circuitry, including a processor and memory, for receiving data, sending data, executing instructions including controlling the voltage applied to the high voltage terminals 222. The high voltage terminals 222 are connected to the windings 220 via conduction lines 236. In some examples, electrical motor/generator 202 and machine drive 204 may comprise a variable frequency drive (VFD).

Signal conditioning module 224 receives input from a plurality of sensors and conditions the high voltage signal to be applied to high voltage terminals 222. For example, environmental measurements from RTDs 212 and 214, air pressure sensor 216, humidity sensor 218, and electrical machine and component measurements such as from dV/dt filter 230, differential mode filter 232, common mode choke 234, and any other measurements from any other sensor, may be received by signal conditioning module 224. Signal conditioning module may then adjust the amplitude, phase, frequency, and waveform shape (sine, square, sawtooth, etc.) of the signal applied to the high voltage terminals 222 based on the received environmental measurements. In some examples, signal conditioning module 224 may adjust received measurements corresponding to partial discharges based on environmental measurements and/or equipment usage factors, and may transmit the conditional signal corresponding to partial discharges to filter stage 226.

Filter stage 226 may receive a signal corresponding to partial discharges, and further condition the signal and/or filter the received signal. For example, filter stage 226 may further condition the received signal by amplifying, offsetting, apodizing, phase shifting, or performing any other operation on the received signal. Filter stage 226 may further filter the received signal by any appropriate technique, for example, high pass filtering the received signal. In some examples, filter stage 226 may filter the received signal in the time domain, and in other examples filter stage 226 may convert the signal to the frequency domain, e.g. via Fourier transform, and filter the signal in the frequency domain. In some examples, filter stage 226 may filter the signal using a low pass filter, a band pass filter, multiple filters of varying type, or any other filter or filtering scheme. Filter stage 226 may determine filtered signal outputs, for example, a filtered version of the received signal, a power spectral density of the filtered signal, or components of the filtered signal such as the parameters of a basis set from which the filtered signal may be reconstructed. Filter stage 226 may transmit filtered signal outputs to insulation health prognostics module 228.

Insulation health prognostics module 228 may receive the filtered signal outputs from filter stage 226, and may determine a partial discharge intensity based on the filtered signal outputs. For example, insulation health prognostics module 228 may determine a partial discharge intensity based on any or all of the amplitude of the received filtered signal, the frequency of the received filtered signal, the duration of the received filtered signal, etc.

In some examples, insultation health prognostics module 228 may correct and/or modify the determined partial discharge intensity based on environmental factors and equipment usage factors, such as further illustrated and described below with respect to FIG. 3. In some examples, insulation health prognostics module 228 may determine if a service alert indicating winding insulation failure or pending winding insulation failure is to be sent based on the partial discharge intensity and/or corrected partial discharge intensity. In the example shown, insulation health prognostics module 228 may transmit a service alert to communication bus 206. Communication bus 206 may allow direct alerts to the cockpit and storage of alerts within the flight computer and/or maintenance tracker.

In some examples, dV/dt filter 230 may control voltage spikes (such as reflected waves) that may occur in variable frequency drives, e.g. electrical motor/generator 202 and machine drive 204. In the example shown, dV/dt filter 230 includes a RC filter for each of the three high voltage lines. In some examples, partial discharges may be measured by monitoring the voltage output of a capacitor connected between a high voltage terminal and chassis ground, such as the capacitors connected between high voltage terminals 222 and ground 210 in the RC filters of dV/dt filter 230. In some embodiments, the capacitors shunt common mode current to ground, and may also shunt partial discharge currents. In the example shown, signal conditioning module 224 may receive input from dV/dt filter 230 corresponding to the high voltage on the capacitors of dV/dt filter 230, thereby monitoring the high voltage on the capacitors for partial discharges. In some embodiments, dV/dt filter 230 and its components are qualified for aircraft and aerospace environments.

In some embodiments, machine drive 204 may include a Y-capacitor electromagnetic interference (Y-Cap EMI) filter (not shown). Y-Cap EMI filters include a capacitor connected between the line and ground, for example, high voltage terminals 222 and ground 210. Y-Cap EMI filters may suppress high frequency common mode voltages of a VFD (and the transmission of high frequency EM waves by the lines 236) by shunting common mode current to ground. The capacitor of a Y-Cap EMI filter may also shunt partial discharge currents. Signal conditioning module 224 may receive input from Y-Cap EMI filters corresponding to the high voltage on the capacitors, thereby monitoring the high voltage on the capacitors for partial discharges. In some embodiments, Y-Cap EMI filters and their components are qualified for aircraft and aerospace environments.

In some examples, machine drive 204 may include high frequency current transformers (HFCTs) connected to each of the high voltage terminals 222. The HFCTs may measure phase currents on the lines 236 to establish closed-loop control. In some examples, HFCTs may include a differential mode filter, such as differential mode filter 232, on each of the lines 236. The example illustrated in FIG. 2 includes one differential mode filter 232 on one of the lines 236, however, in some examples a differential mode filter 232 may be connected on one or more of the lines 236. A HFCT with differential mode filter 232 and a relatively high bandwidth may also be used to measure the partial discharges. Signal conditioning module 224 may receive input from differential mode filter 232, thereby monitoring the high voltage lines 236 for partial discharges. In some embodiments, HFTCs incorporating differential mode filter 232 and their components are qualified for aircraft and aerospace environments.

In some examples, HFCTs connected to each of the high voltage terminals 222 may include a common mode choke, such as common mode choke 234, on each of the lines 236. Common mode choke 234 may be comprised of a magnetic core enclosing the three phase outputs, e.g. the lines 236. A wire may be wrapped around the magnetic core to form a common mode current transformer. Including a HFCT to measure common mode current may also function as a common mode choke. Signal conditioning module 224 may receive input from common mode choke 234, thereby monitoring the high voltage lines 236 for partial discharges. In some embodiments, common mode choke 234 and its components are qualified for aircraft and aerospace environments.

In some examples, HFCT 240 may be included on bond straps used to connect electrical machines or other components to ground, for example bond strap 208 connecting electrical motor/generator 202 to ground 210. HFCT 240 may be configured to measure the current between the electrical machine and/or component, e.g. electrical motor/generator 202, and ground 210. Signal conditioning module 224 may receive input from HFCT 240, thereby monitoring the grounding current for partial discharges. In some embodiments, HFCT 240 and its components are qualified for aircraft and aerospace environments.

In some examples, electric motor/generator 202 includes one or more sensors, for example, resistance temperature sensors (RTDs) 212 and 214. RTDs 212 and 214 may be monitored by machine drive 204 to detect overheating. In some examples, the voltage output by RTDs 212 and 214 may contain high frequency components corresponding to partial discharges. Signal conditioning module 224 may receive input from RTDs 212 and 214, thereby monitoring the voltage output from RTDs 212 and 214 for partial discharges. In some embodiments, RTDs 212 and 214 are qualified for aircraft and aerospace environments.

In some examples, partial discharges may vary depending on environmental conditions and equipment usage factors. For example, the inputs received by signal conditioning module 224 may vary depending on environmental conditions and equipment usage factors, and such variation may be received by insulation health prognostics module 228 and may cause variation in partial discharge intensity determined by insulation health prognostics module 228. In some examples, partial discharge monitoring system 200 may include a partial discharge intensity correction system, for example, a partial discharge intensity correction system may be implemented by insulation health prognostics module 228. In other example, a partial discharge intensity correction system may be implemented by machine drive 204, or anywhere in partial discharge monitoring system 200.

Figure 3:
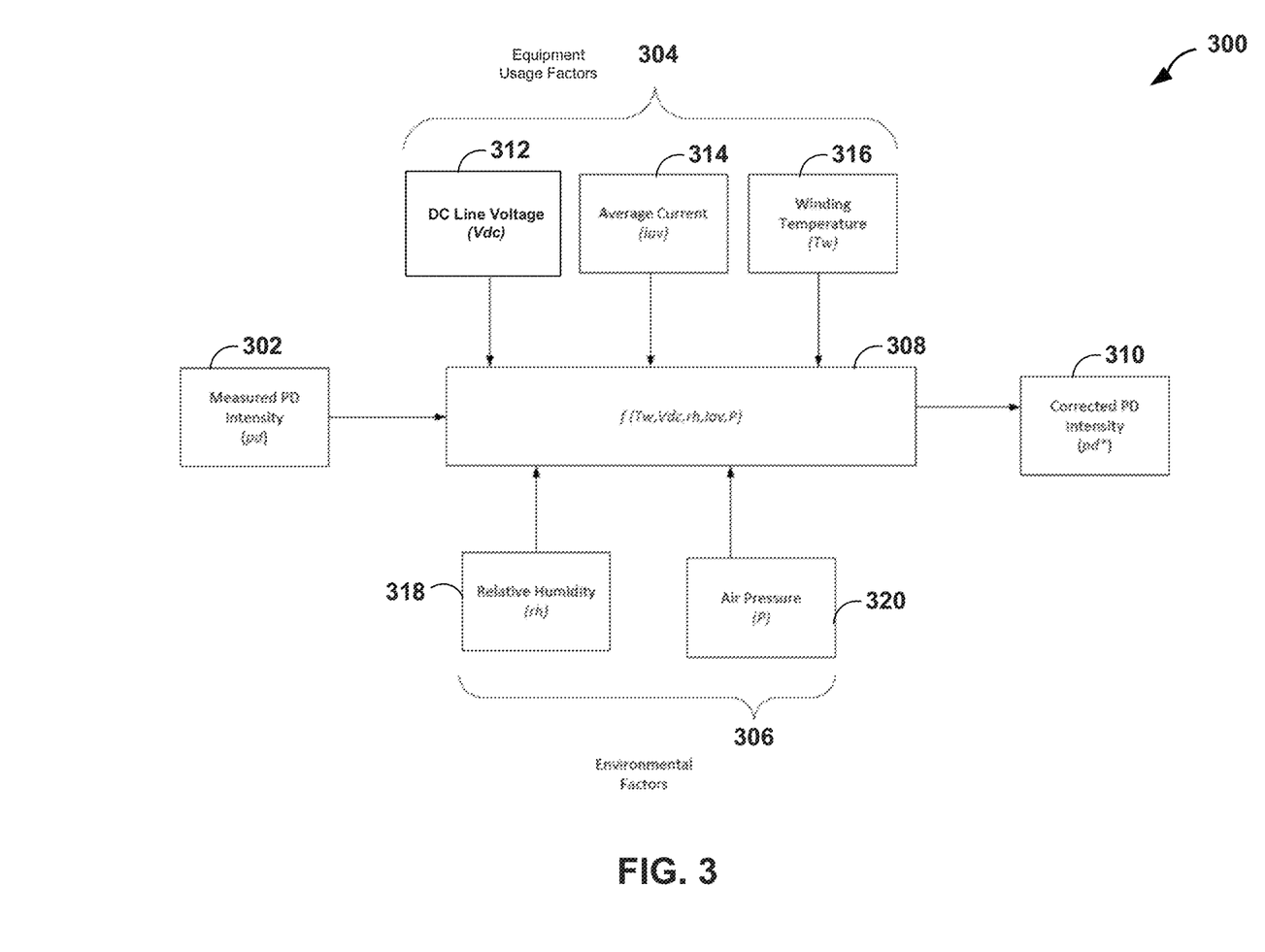
FIG. 3 is a conceptual diagram illustrating an example partial discharge intensity correction system, in accordance with one or more techniques of this disclosure.

FIG. 3 is a conceptual diagram illustrating an example partial discharge intensity correction system 300, in accordance with one or more techniques of this disclosure. In the example shown, system 300 includes a partial discharge intensity 302, equipment usage factors 304, environmental measurements 306, correction module 308, and corrected partial discharge intensity 310. Partial discharge intensity correction system 300 may be implemented via machine drive 204, for example, by insulation health prognostics module 228.

In the example shown, insulation health prognostics module 228 may determine partial discharge intensity 302, for example, based on a filtered signal from filter stage 226 as described above with respect to FIG. 2. In some examples, partial discharge intensity 302 may be a value, e.g. a quantity, representing a partial discharge.

In the example shown, equipment usage factors 304 may include direct current (DC) line voltage (Vdc) 312, average line current 314, and winding temperature 316. In some examples, equipment usage factors 304 may include additional equipment usage factors. In the example shown, DC line voltage 312 and average line current 314 correspond to the voltage and average current, respectively, on conduction lines 236 connected to windings 220 at or near the time a partial discharge occurs, e.g. the partial discharge event on which the partial discharge intensity 302 being corrected is based. Similarly, winding temperature 316 corresponds to the temperature of windings 220 at or near the time a partial discharge occurs, e.g. the partial discharge event on which the partial discharge intensity 302 being corrected is based.

In the example shown, environmental measurements 306 may include relative humidity (RH) measurement 318 and air pressure measurement 320. For example, RH measurement 318 and air pressure measurement 320 may be measurements within the housing of electrical motor/generator 202 in which the windings 220 reside. In the example shown, RH measurement 318 and air pressure measurement 320 correspond to the RH and air pressure, respectively, at or near windings 220 and at or near the time a partial discharge occurs, e.g. the partial discharge event on which the partial discharge intensity 302 being corrected is based.

In the example shown, correction module 308 may receive partial discharge intensity 302, equipment usage factors 304, and environmental measurements 306. In some examples, correction module 308 may modify the value, or quantity, of partial discharge intensity 302 based on one or more of equipment usage factors 304 and environmental measurements 306 and output corrected partial discharge intensity 312. For example, if the RH at or near windings 220 increases, any of the amplitude, frequency, and/or duration of partial discharges may increase relative to partial discharges at a lower RH, resulting in an increased partial discharge intensity 302 relative to partial discharge intensity 302 at a lower RH. In other words, the partial discharge intensity 302 may be based on both an environmental factor, the RH, and the health of the insulation of windings 220. As such, partial discharge intensity 302 may vary due to factors other than insulation health, e.g. RH. Correction module 308 may modify partial discharge intensity 302 based on RH measurement 318, e.g. correction module 308 may output a corrected partial discharge intensity 310 that is lower than partial discharge intensity 302 based on the higher RH measurement 318. In some examples, if the RH decreases at or near windings 220, correction module 308 may output a corrected partial discharge intensity 310 that is higher than partial discharge intensity 302 based on the lower RH measurement 318.

In some examples, if air pressure 320 at or near windings 220 decreases, any of the amplitude, frequency, and/or duration of partial discharges may increase, resulting in an increased partial discharge intensity 302. Correction module 308 may modify partial discharge intensity 302 based on air pressure measurement 320, e.g. correction module 308 may output a corrected partial discharge intensity 310 that is lower than partial discharge intensity 302 based on the lower air pressure measurement 320. In some examples, if the air pressure decreases at or near windings 220, correction module 308 may output a corrected partial discharge intensity 310 that is higher than partial discharge intensity 302 based on the higher air pressure measurement 320.

In some examples, if any of DC line voltage 312, average current 314, and winding temperature 316 increase, any of the amplitude, frequency, and/or duration of partial discharges may increase, resulting in an increased partial discharge intensity 302. Correction module 308 may modify partial discharge intensity 302 based on DC line voltage 312, average current 314, and winding temperature 316, e.g. correction module 308 may output a corrected partial discharge intensity 310 that is lower than partial discharge intensity 302 based on DC line voltage 312, average current 314, and winding temperature 316. In some examples, if any of DC line voltage 312, average current 314, and winding temperature 316 decrease, correction module 308 may output a corrected partial discharge intensity 310 that is higher than partial discharge intensity 302 based on the lower DC line voltage 312, average current 314, and winding temperature 316.

In some examples, correction module 308 may modify the value of partial discharge intensity 302 based on one or more additional equipment usage factors and/or environmental measurements alone or in combination with equipment usage factors 304 and environmental measurements 306.

In the example shown, corrected partial discharge intensity 310 may be corrected such that variations of partial discharge intensity 302 based on environmental conditions and/or factors and equipment usage factors have been substantially reduced or eliminated. For example, corrected partial discharge intensity 310 may include variations based substantially only on the health of the insulation of windings 220, e.g. the insulating properties of the insulation of windings 220.

In some examples, the health of insulation may be determined based on changes in corrected partial discharge intensity 310 over time. For example, a baseline corrected partial discharge intensity level, e.g. value or quantity, may be determined corresponding to any or either of an initial, expected, or normal corrected partial discharge intensity level.

Figure 4:
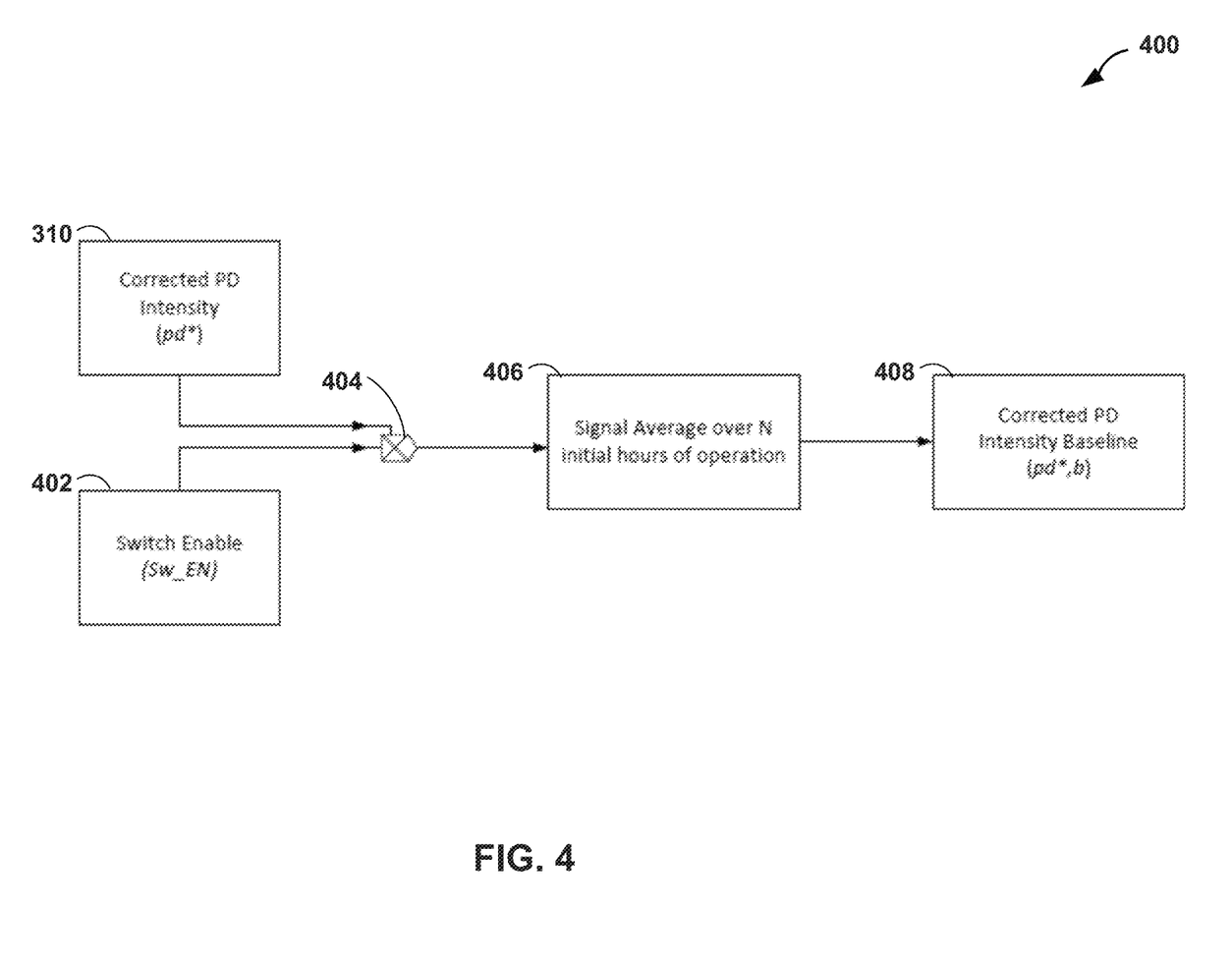
FIG. 4 is a conceptual diagram illustrating an example partial discharge intensity baselining system, in accordance with one or more techniques of this disclosure.

FIG. 4 is a conceptual diagram illustrating an example partial discharge intensity baselining system 400, in accordance with one or more techniques of this disclosure. In the example shown, system 400 includes corrected partial discharge intensity 310, switch enable 402, switch 404, signal average 406 module, and corrected partial discharge intensity baseline 408. System 400 may be implemented via machine drive 204, for example, by insulation health prognostics module 228.

In the example shown, switch enable 402 may include signal sent to switch 404 to enable collection of corrected partial discharge intensity 310, for example, over a period of time and/or number of corrected partial discharge intensity values. In some examples, switch enable may control switch 404. In some examples, switch enable 402 may be selected, e.g. to turn switch 404 "on" and/or "off," by a user, e.g. at a user interface of partial discharge monitoring system 200, for example a user interface in the cockpit of an aircraft configured to receive user input for control of machine drive 204. In other examples, machine drive 204 may select switch enable 402 to turn switch 404 "on" and/or "off," for example via instructions stored in computer memory in the processing circuitry of machine drive 204 and executed by one or more processors. In some examples, switch enable 402 may be selected to turn switch 404 "on" for a predetermined period of time and/or a predetermined number of corrected partial discharge values when a power converter is actively powering its device, e.g. a power converter of partial discharge monitoring system 200 powering electric motor/generator 202. In some examples, the predetermined period of time and/or number of corrected partial discharge values includes the first, e.g. initial, hours or number of corrected partial discharge values that electric motor/generator 202 is powered. In some examples, switch enable 402 may be turn switch 404 "off" such that when electric motor/generator 202 is not powered, or by a user, or for any reason, corrected partial discharge intensity 310 values are not sent to signal average module 406

In the example shown, signal average module 406 may receive corrected partial discharge intensity 310 values when switch 404 is "on." In some examples, signal average module 406 may calculate an average corrected partial discharge intensity value, for example, the average corrected partial discharge intensity of the predetermined initial hours, or number of corrected partial discharge intensity values, of operation of electric motor/generator 202. In some examples, the average corrected partial discharge intensity may comprise corrected partial discharge intensity baseline 408. In some examples, corrected partial discharge intensity baseline 408 may be a value stored in memory, for example, within processing circuitry of machine drive 204.

In some examples, partial discharge monitoring system 200 may be configured to determine insulation health via comparison of a current measured corrected partial discharge intensity, e.g. corrected partial discharge intensity 310, with corrected partial discharge intensity baseline 408.

Figure 5:
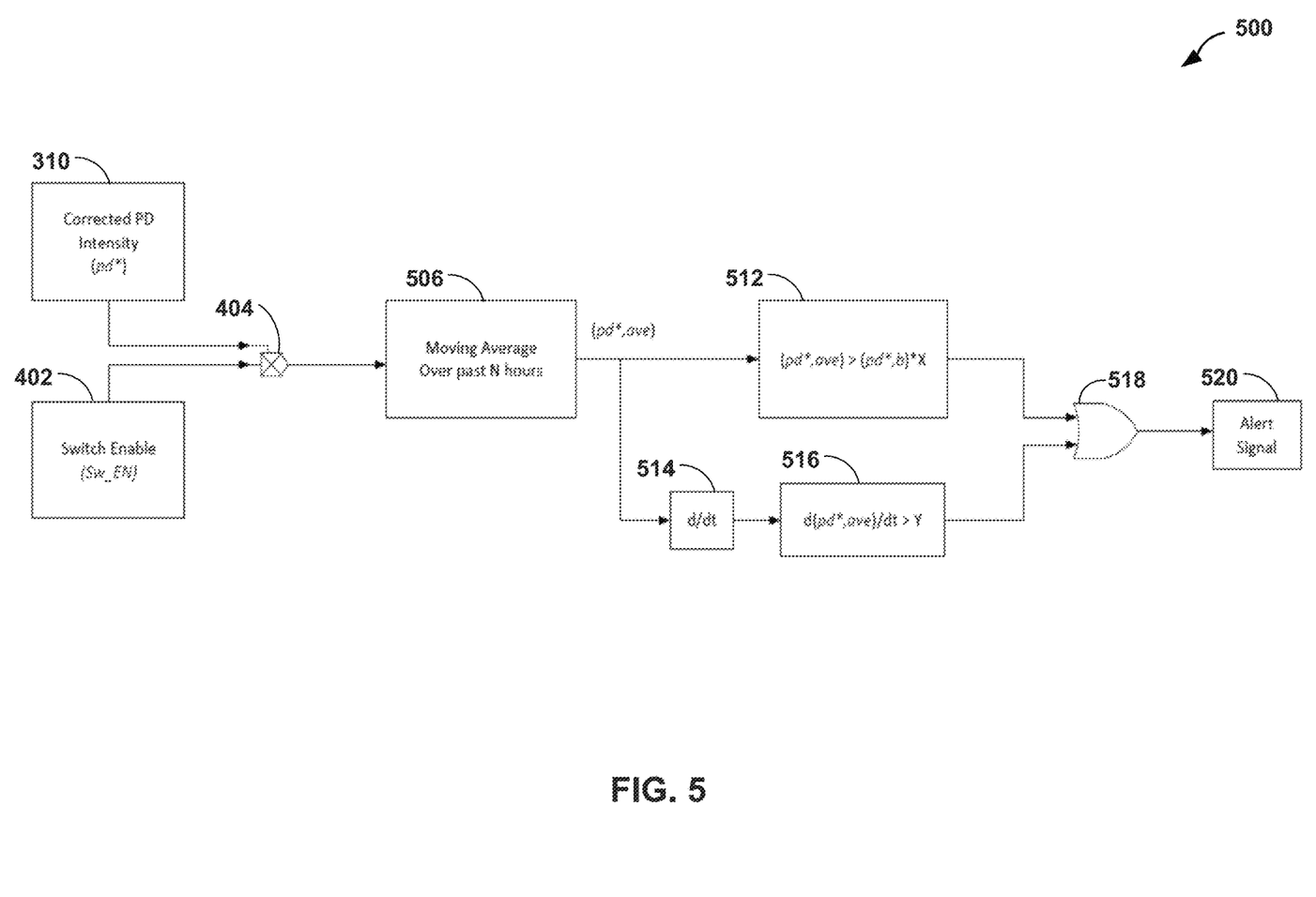
FIG. 5 is a conceptual diagram illustrating an example partial discharge intensity alert signal generation system, in accordance with one or more techniques of this disclosure.

FIG. 5 is a conceptual diagram illustrating an example partial discharge intensity alert signal generation system 500, in accordance with one or more techniques of this disclosure. In the example shown, system 500 includes corrected partial discharge intensity 310, switch enable 402, switch 404, moving average 506 module, comparison module 512, time derivative module 514, rate change comparison module 516, logical OR gate 518, and alert signal 520. System 500 may be implemented via machine drive 204, for example, by insulation health prognostics module 228.

In the example shown, switch enable 402 may include a signal sent to switch 404 to enable collection of corrected partial discharge intensity 310 as described above with respect to FIG. 4. In some examples, switch enable 402 may be configured to control switch 404 "on" or "off" during any time, rather than just for collection of corrected partial discharge intensity 310 values during initial operation of electric motor/generator 202.

In the example shown, moving average module 506 may receive corrected partial discharge intensity 310 values when switch 404 is "on." In some examples, moving average module 506 may calculate an average corrected partial discharge intensity value, for example, the average corrected partial discharge intensity of a predetermined number of hours, or number of corrected partial discharge intensity values, of operation of electric motor/generator 202.

In the example shown, comparison module 512 may generate an alert signal 520 based on a comparison of the average corrected partial discharge intensity value calculated via moving average module 506 with corrected partial discharge intensity baseline 408. For example, if the average corrected partial discharge intensity value is greater than partial discharge intensity baseline 408, comparison module 512 may generate alert signal 520, whereas if the average corrected partial discharge intensity value is less than or equal to corrected partial discharge intensity baseline 408, comparison module 512 may not generate alert signal 520. In some examples, comparison module 512 may multiply corrected partial discharge intensity baseline 408 by a factor X, for example, where X may be a numerical factor such as 1.1, 0.5, 2.0, 3.0, or any other numerical factor, before comparing corrected partial discharge intensity baseline 408 with the average corrected partial discharge intensity. For example, if the average corrected partial discharge intensity value is greater than twice the partial discharge intensity baseline 408 (e.g. X=2.0), comparison module 512 may generate alert signal 520, whereas if the average corrected partial discharge intensity value is less than or equal to twice the corrected partial discharge intensity baseline 408, comparison module 512 may not generate alert signal 520. In some examples, factor X may be determined empirically, for example, via experience or past history of service and maintenance of electric motor/generator 202 or comparable electric motors/generators (e.g. of same or similar design).

In the example shown, time derivative module 514 may determine a rate of change of the average corrected partial discharge intensity value determined by moving average module 506. For example, time derivative module 514 may receive a plurality of average corrected partial discharge intensity values over a period of time and determine a rate of change of the average corrected partial discharge intensity values over time. In some examples, the rate of change may be instantaneous, for example, the rate of change between two consecutive average corrected partial discharge intensity values, and in some examples the rate of change may be with respect to a plurality of average corrected partial discharge intensity values over a period of time.

In the example shown, rate change comparison module 516 may generate an alert signal 520 based on a comparison of the rate of change of the average corrected partial discharge intensity value calculated via rate change module 514 with a rate change factor Y. For example, if the rate of change of average corrected partial discharge intensity values is greater than rate change factor Y, rate change comparison module 516 may generate alert signal 520, whereas if the rate of change of the average corrected partial discharge intensity values is less than or equal to rate change factor Y, rate change comparison module 516 may not generate alert signal 520. In some examples, rate change factor Y may be determined empirically, for example, via experience or past history of service and maintenance of electric motor/generator 202 or comparable electric motors/generators (e.g. of same or similar design).

In the example shown, alert signal 520 generated by one or both of comparison module 512 and rate change comparison module 516 may be combined, e.g. via logical OR gate 518, into a combined alert signal 520. In some examples, combined alert signal 520 may be received at a user interface of partial discharge monitoring system 200, for example a user interface in the cockpit of an aircraft configured to display outputs from partial discharge monitoring system 200 and receive user input for control of machine drive 204.

Figure 6:
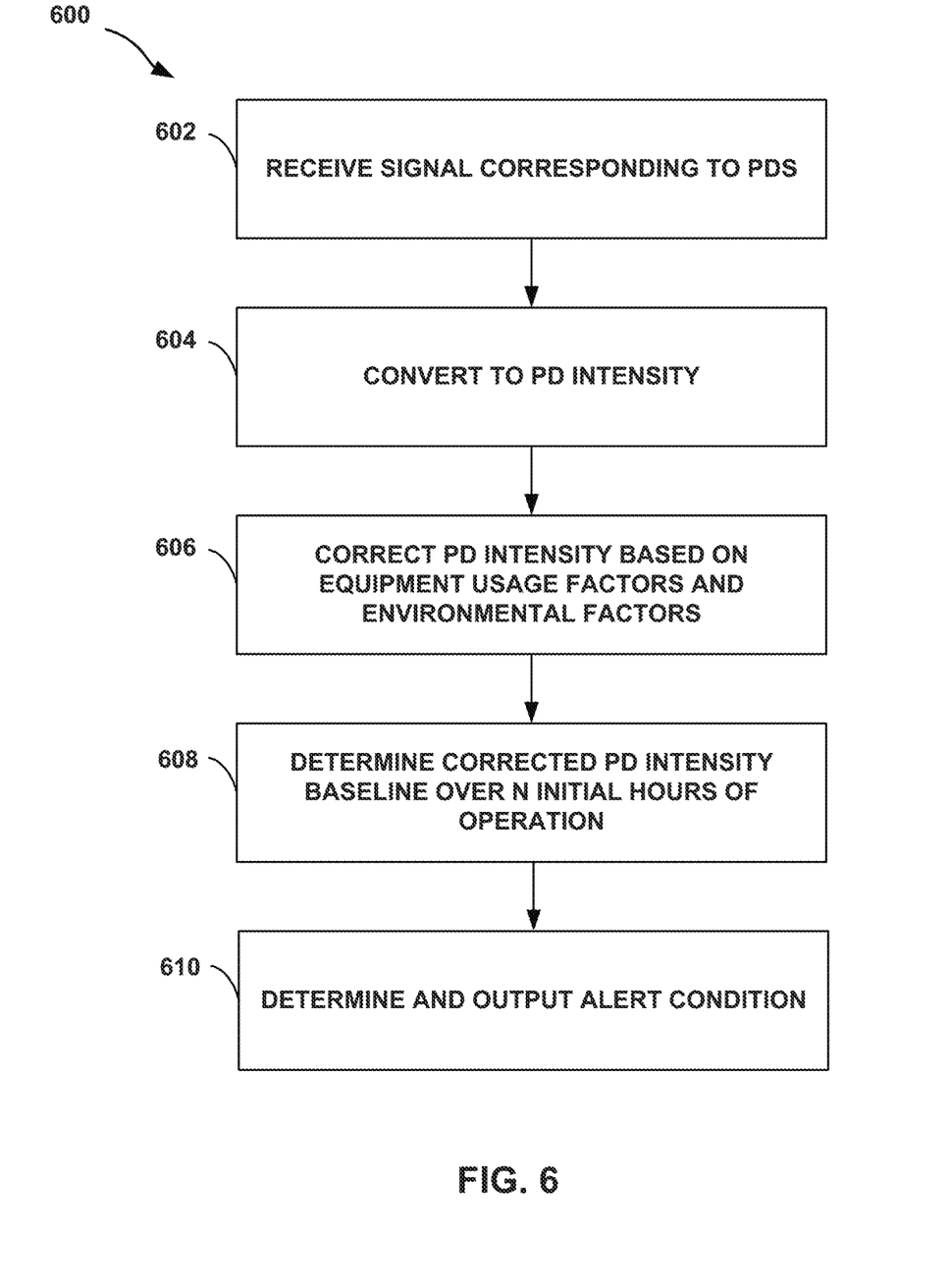
FIG. 6 is a flowchart of an example method of monitoring partial discharge intensity, in accordance with one or more techniques of this disclosure.

FIG. 6 is a flowchart of an example method 600 of monitoring partial discharge intensity, in accordance with one or more techniques of this disclosure. The example method is described with respect to partial discharge monitoring system 200 of FIGS. 2-5.

At receive signal corresponding to partial discharges step 602, signal conditioning module 224 may receive input, e.g. signals corresponding to partial discharge, from a plurality of sensors. For example, signal conditioning module may execute instructions stored in memory via a processor of processing circuitry included in machine drive 204 to receive input corresponding to operational characteristics of a device, e.g. partial discharges from one or more of RTDs 212 and 214, dV/dt filter 230, differential mode filter 232, common mode choke 234, and HFCT 240. In some examples, any or all of RTDs 212 and 214, dV/dt filter 230, differential mode filter 232, common mode choke 234, and HFCT 240 may be included in electrical motor/generator 202 and motor drive 204 and already existing for other purposes, e.g. for driving and/or correcting voltages and/or signals applied to HV terminals 222 for operating electric motor/generator 202, and partial discharge monitoring system 200 may utilize any or all of RTDs 212 and 214, dV/dt filter 230, differential mode filter 232, common mode choke 234, and HFCT 240 to additionally provide inputs corresponding to partial discharges.

At convert to partial discharge intensity step 604, signal conditioning module 224 may condition (e.g. adjust) received inputs (e.g. signals and/or measurements) corresponding to partial discharges based on environmental measurements and/or equipment usage factors, and may transmit the conditioned signal corresponding to partial discharges to filter stage 226. For example, signal conditioning module may receive measurements of air pressure and relative humidity, and equipment usage factors such as DC line voltage of lines 236, average current of lines 236, and the temperature of windings 220, and condition the received inputs based on such environmental measurements and equipment usage factors. Filter stage 226 may further condition the conditioned inputs via amplification, filtering, etc., as described above with respect to FIG. 2. Insulation health prognostics module 228 may then receive the filtered signal outputs from filter stage 226 and may determine a partial discharge intensity based on the filtered signal outputs, as described above with respect to FIGS. 2-3.

At correct partial discharge intensity step 606, insulation health prognostics module 228 may correct, e.g. modify, the determined partial discharge intensity based on environmental measurements and equipment usage factors as described above with respect to FIG. 3.

At determine corrected partial discharge intensity baseline step 608, insulation health prognostics module 228 may determine a baseline corrected partial discharge intensity, for example, a baseline corrected partial discharge intensity of the initial operation of electrical motor/generator 202 as described above with respect to FIG. 4.

At determine and output alert condition step 610, insulation health prognostics module 228 may determine an alert signal, and output the alert signal, based on a comparison of one or more corrected partial discharge intensity values to the determined corrected partial discharge intensity baseline and/or a comparison of the rate of change of corrected partial discharge intensity values to a rate change factor as described above with respect to FIG. 5.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in an article of manufacture including a computer-readable storage medium encoded with instructions. Instructions embedded or encoded in an article of manufacture including a computer-readable storage medium, may cause one or more programmable processors, or other processors, to implement one or more of the techniques described herein, such as when instructions included or encoded in the computer-readable storage medium are executed by the one or more processors. Computer readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

The following examples may illustrate one or more aspects of the disclosure:

Example 1. A method comprising: receiving, by one or more processors and via a sensor, a signal representing operational characteristics of a device included in an aircraft; determining, by the one or more processors and based on the signal, a partial discharge intensity value; receiving, by the one or more processors and via an environmental sensor, at least one environmental measurement of the device; modifying, by the one or more processors and based on the at least one environmental measurement, the partial discharge intensity value to determine a modified partial discharge intensity value; and responsive to determining that the modified partial discharge intensity value satisfies a threshold, outputting an alert signal for the device.

Example 2. The method of example 1, wherein modifying the partial discharge intensity value further comprises modifying the partial discharge intensity value based on at least one equipment usage factor.

Example 3. The method of example 2, wherein the at least one equipment usage factor includes one or more of a direct current (DC) line voltage, an average conductor coil current, and a winding temperature.

Example 4. The method of any of examples 1-3, wherein the at least one environmental measurement comprises one or more of a relative humidity and an air pressure.

Example 5. The method of example 3, wherein the device included in the aircraft includes a conductor driven with a variable frequency current.

Example 6. The method of any of examples 1-5, wherein the sensor comprises one or more of a resistance temperature sensor, a high frequency current transformer, a common mode high frequency current transformer, a voltage derivative sensor, and a Y capacitor.

Example 7. The method of any of examples 1-6, wherein determining the modified partial discharge intensity value comprises determining a plurality of modified partial discharge intensity values that each correspond to a different time during a time period, wherein determining whether the modified partial discharge value satisfies the threshold comprises determining whether the plurality of modified partial discharge intensity values satisfy the threshold.

Example 8. The method of example 7, wherein determining whether the plurality of modified partial discharge intensity values satisfy the threshold comprises determining whether a rate of change of the plurality of modified partial discharge intensity values is greater than a threshold rate of change.

Example 9. The method of any of examples 7-8, wherein the plurality of modified partial discharge intensity values comprises a first plurality of modified partial discharge intensity values for a first time period, the method further comprising: determining, based on a plurality of modified partial discharge intensity values for a second time period that is before the first time period, a baseline modified partial discharge intensity value, wherein determining whether the plurality of modified partial discharge intensity values satisfy the threshold comprises determining whether an average of the first plurality of modified partial discharge intensity values is greater than a scaled version of the baseline modified partial discharge intensity value.

Example 10. A system comprising: a device included in an aircraft; an environmental sensor; a sensor; and one or more processors configured to: receive, via the sensor, a signal representing operational characteristics of a device included in an aircraft; determine, based on the signal, a partial discharge intensity value; receive, via the environmental sensor, at least one environmental measurement of the device; modify, based on the at least one environmental measurement, the partial discharge intensity value to determine a modified partial discharge intensity value; and responsive to determining that the modified partial discharge intensity value satisfies a threshold, output an alert signal for the device.

Example 11. The system of example 10, wherein modifying the partial discharge intensity value further comprises modifying the partial discharge intensity value based on at least one equipment usage factor.

Example 12. The system of example 11, wherein the sensor comprises one or more of a resistance temperature sensor, a high frequency current transformer, a common mode high frequency current transformer, a voltage derivative sensor, and a Y capacitor, and wherein the at least one equipment usage factor includes one or more of a direct current (DC) line voltage, an average conductor coil current, and a winding temperature.

Example 13. The system of any of examples 10-12, wherein the at least one environmental measurement comprises one or more of a relative humidity and an air pressure.

Example 14. The system of any of examples 10-13, wherein determining the modified partial discharge intensity value comprises determining a plurality of modified partial discharge intensity values that each correspond to a different time during a time period, wherein determining whether the modified partial discharge value satisfies the threshold comprises at least one of determining whether the plurality of modified partial discharge intensity values satisfy the threshold and determining whether a rate of change of the plurality of modified partial discharge intensity values is greater than a threshold rate of change.

Example 15. The system of example 14, wherein the plurality of modified partial discharge intensity values comprises a first plurality of modified partial discharge intensity values for a first time period, the one or more processors further configured to: determine, based on a plurality of modified partial discharge intensity values for a second time period that is before the first time period, a baseline modified partial discharge intensity value, wherein determining whether the plurality of modified partial discharge intensity values satisfy the threshold comprises determining whether an average of the first plurality of modified partial discharge intensity values is greater than a scaled version of the baseline modified partial discharge intensity value.

Example 16. A variable frequency drive system comprising: an electric machine; one or more conductor coils; an environmental sensor; a sensor; and at least variable frequency drive configured to provide electrical power to the electric machine, the at least variable frequency drive comprising: at least one high voltage terminal; and at least one processor configured to: receive, via the sensor, a signal representing operational characteristics of the variable frequency drive system; determine, based on the signal, a partial discharge intensity value; receive, via the environmental sensor, at least one environmental measurement of the variable frequency drive system; modify, based on the at least one environmental measurement, the partial discharge intensity value to determine a modified partial discharge intensity value; and responsive to determining that the modified partial discharge intensity value satisfies a threshold, output an alert signal for the device.

Example 17. The variable frequency drive system of examples 16, wherein modifying the partial discharge intensity value further comprises modifying the partial discharge intensity value based on at least one equipment usage factor.

Example 18. The variable frequency drive system of any of examples 16-17, wherein the at least one environmental measurement comprises one or more of a relative humidity and an air pressure.

Example 19. The variable frequency drive system of example 18, wherein the sensor comprises one or more of a resistance temperature sensor, a high frequency current transformer, a common mode high frequency current transformer, a voltage derivative sensor, and a Y capacitor, and wherein the at least one equipment usage factor includes one or more of a direct current (DC) line voltage, an average conductor coil current, and a winding temperature.

Example 20. The variable frequency drive system of any of examples 16-19, wherein determining the modified partial discharge intensity value comprises determining a plurality of modified partial discharge intensity values that each correspond to a different time during a time period, wherein determining whether the modified partial discharge value satisfies the threshold comprises at least one of determining whether the plurality of modified partial discharge intensity values satisfy the threshold and determining whether a rate of change of the plurality of modified partial discharge intensity values is greater than a threshold rate of change.

Various examples have been described. These and other examples are within the scope of the following claims.

What is claimed is:

1. A method comprising:
   receiving, by one or more processors and via a sensor, a signal representing operational characteristics of a device included in an aircraft;
   determining, by the one or more processors and based on the signal, a partial discharge intensity value;
   receiving, by the one or more processors and via an environmental sensor, at least one environmental measurement of the device;
   modifying, by the one or more processors and based on the at least one environmental measurement, the partial discharge intensity value to determine a modified partial discharge intensity value; and
   responsive to determining that the modified partial discharge intensity value satisfies a threshold, outputting an alert signal for the device.

2. The method of claim 1, wherein modifying the partial discharge intensity value further comprises modifying the partial discharge intensity value based on at least one equipment usage factor.

3. The method of claim 2, wherein the at least one equipment usage factor includes one or more of a direct current (DC) line voltage, an average conductor coil current, and a winding temperature.

4. The method of claim 1, wherein the at least one environmental measurement comprises one or more of a relative humidity and an air pressure.

5. The method of claim 3, wherein the device included in the aircraft includes a conductor driven with a variable frequency current.

6. The method of claim 1, wherein the sensor comprises one or more of a resistance temperature sensor, a high frequency current transformer, a common mode high frequency current transformer, a voltage derivative sensor, and a Y capacitor.

7. The method of claim 1, wherein determining the modified partial discharge intensity value comprises determining a plurality of modified partial discharge intensity values that each correspond to a different time during a time period, wherein determining whether the modified partial discharge value satisfies the threshold comprises determining whether the plurality of modified partial discharge intensity values satisfy the threshold.

8. The method of claim 7, wherein determining whether the plurality of modified partial discharge intensity values satisfy the threshold comprises determining whether a rate of change of the plurality of modified partial discharge intensity values is greater than a threshold rate of change.

9. The method of claim 7, wherein the plurality of modified partial discharge intensity values comprises a first plurality of modified partial discharge intensity values for a first time period, the method further comprising:
   determining, based on a plurality of modified partial discharge intensity values for a second time period that is before the first time period, a baseline modified partial discharge intensity value,
   wherein determining whether the plurality of modified partial discharge intensity values satisfy the threshold comprises determining whether an average of the first plurality of modified partial discharge intensity values is greater than a scaled version of the baseline modified partial discharge intensity value.

10. A system comprising:
    a device included in an aircraft;
    an environmental sensor;
    a sensor; and
    one or more processors configured to:
       receive, via the sensor, a signal representing operational characteristics of a device included in an aircraft;
       determine, based on the signal, a partial discharge intensity value;
       receive, via the environmental sensor, at least one environmental measurement of the device;
       modify, based on the at least one environmental measurement, the partial discharge intensity value to determine a modified partial discharge intensity value; and
       responsive to determining that the modified partial discharge intensity value satisfies a threshold, output an alert signal for the device.

11. The system of claim 10, wherein modifying the partial discharge intensity value further comprises modifying the partial discharge intensity value based on at least one equipment usage factor.

12. The system of claim 11, wherein the sensor comprises one or more of a resistance temperature sensor, a high frequency current transformer, a common mode high frequency current transformer, a voltage derivative sensor, and a Y capacitor, and
    wherein the at least one equipment usage factor includes one or more of a direct current (DC) line voltage, an average conductor coil current, and a winding temperature.

13. The system of claim 10, wherein the at least one environmental measurement comprises one or more of a relative humidity and an air pressure.

14. The system of claim 10, wherein determining the modified partial discharge intensity value comprises determining a plurality of modified partial discharge intensity values that each correspond to a different time during a time period, wherein determining whether the modified partial discharge value satisfies the threshold comprises at least one of determining whether the plurality of modified partial discharge intensity values satisfy the threshold and determining whether a rate of change of the plurality of modified partial discharge intensity values is greater than a threshold rate of change.

15. The system of claim 14, wherein the plurality of modified partial discharge intensity values comprises a first plurality of modified partial discharge intensity values for a first time period, the one or more processors further configured to:
- determine, based on a plurality of modified partial discharge intensity values for a second time period that is before the first time period, a baseline modified partial discharge intensity value,
- wherein determining whether the plurality of modified partial discharge intensity values satisfy the threshold comprises determining whether an average of the first plurality of modified partial discharge intensity values is greater than a scaled version of the baseline modified partial discharge intensity value.

16. A variable frequency drive system comprising:
an electric machine;
one or more conductor coils;
an environmental sensor;
a sensor; and
at least variable frequency drive configured to provide electrical power to the electric machine, the at least variable frequency drive comprising:
  at least one high voltage terminal; and
  at least one processor configured to:
    receive, via the sensor, a signal representing operational characteristics of the variable frequency drive system;
    determine, based on the signal, a partial discharge intensity value;
    receive, via the environmental sensor, at least one environmental measurement of the variable frequency drive system;
    modify, based on the at least one environmental measurement, the partial discharge intensity value to determine a modified partial discharge intensity value; and
    responsive to determining that the modified partial discharge intensity value satisfies a threshold, output an alert signal for the device.

17. The variable frequency drive system of claim 16, wherein modifying the partial discharge intensity value further comprises modifying the partial discharge intensity value based on at least one equipment usage factor.

18. The variable frequency drive system of claim 17, wherein the at least one environmental measurement comprises one or more of a relative humidity and an air pressure.

19. The variable frequency drive system of claim 18, wherein the sensor comprises one or more of a resistance temperature sensor, a high frequency current transformer, a common mode high frequency current transformer, a voltage derivative sensor, and a Y capacitor, and
wherein the at least one equipment usage factor includes one or more of a direct current (DC) line voltage, an average conductor coil current, and a winding temperature.

20. The variable frequency drive system of claim 16, wherein determining the modified partial discharge intensity value comprises determining a plurality of modified partial discharge intensity values that each correspond to a different time during a time period, wherein determining whether the modified partial discharge value satisfies the threshold comprises at least one of determining whether the plurality of modified partial discharge intensity values satisfy the threshold and determining whether a rate of change of the plurality of modified partial discharge intensity values is greater than a threshold rate of change.

* * * * *